US007319467B2

(12) United States Patent
Weyrich et al.

(10) Patent No.: US 7,319,467 B2
(45) Date of Patent: Jan. 15, 2008

(54) SKIN REFLECTANCE MODEL FOR REPRESENTING AND RENDERING FACES

(75) Inventors: Tim Weyrich, Zurich (CH); Wojciech Matusik, Cambridge, MA (US); Hanspeter Pfister, Arlington, MA (US); Henrik Wann Jensen, Santa Monica, CA (US); Wai Kit Addy Ngan, Cambridge, MA (US); Markus Gross, Uster (CH)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 222 days.

(21) Appl. No.: 11/092,426

(22) Filed: Mar. 29, 2005

(65) Prior Publication Data

US 2006/0227137 A1 Oct. 12, 2006

(51) Int. Cl.
*G06T 15/50* (2006.01)
(52) U.S. Cl. ..................................................... 345/426
(58) Field of Classification Search ..................... None
See application file for complete search history.

(56) References Cited

U.S. PATENT DOCUMENTS 5,258,925 A * 11/1993 Maier et al. ................ 382/112
6,342,885 B1 * 1/2002 Knittel et al. ............... 345/424
6,639,594 B2 * 10/2003 Zhang et al. ................ 345/426
2004/0227948 A1 * 11/2004 Debevec et al. ............ 356/445
2006/0214931 A1 * 9/2006 Snyder et al. .............. 345/426

OTHER PUBLICATIONS

Matusik et al. A Data-Driven Reflectance Model. ACM Transactions on Graphics. vol. 22. Issue 3. Jul. 2003.*
Jensen et al. A Practical Model for Subsurface Light Transport. Proceedings of the 28th Annual Conference on Computer Graphics and Interactive Techniques. 2001.*
Gardner et al. Linear Light Source Reflectometry. ACM Transactions on Graphics. vol. 22. Issue 3. Jul. 2003.*

* cited by examiner

*Primary Examiner*—Kee M Tung
*Assistant Examiner*—Peter-Anthony Pappas
(74) *Attorney, Agent, or Firm*—Dirk Brinkman; Clifton D. Mueller; Gene V. Vinokur (57) ABSTRACT

A face is scanned to obtain a three-dimensional geometry of the face, images are also acquired of the face, and subsurface scattering of the face is measured. A translucency map is determined from the subsurface reflectance. A total surface reflectance and a normal map are estimated from the three-dimensional geometry and the images, and diffuse reflectance is estimated using the total reflectance. An albedo map is determined from the diffuse reflectance. The diffuse reflectance is subtracted from the total reflectance to obtain a surface reflectance. A set of bi-directional reflectance functions is fitted to the surface reflectance. Then, the set of bi-directional reflectance distribution functions, the albedo map, and the translucency map are combined to form a skin reflectance model of the face.

12 Claims, 5 Drawing Sheets

SKIN REFLECTANCE MODEL FOR REPRESENTING AND RENDERING FACES

FIELD OF THE INVENTION

This invention is generally related to rendering faces using computer graphics, and more particularly to modeling skin reflectance, and editing the skin reflectance models to render synthetic images.

BACKGROUND OF THE INVENTION

One of the most difficult computer graphics challenges is rendering realistic human faces. Humans are incredibly adept at interpreting facial appearance. For example, we can easily distinguish if a person is happy, tired, hot, angry, excited, or sick. Although a lot of effort has been devoted to face modeling in computer graphics, no synthetic face model to date achieves the level of expressiveness of human faces.

Realism requires an accurate model for the skin reflectance of human faces. Skin reflectance varies for different people, e.g., due to age, race, gender, health, etc. Skin reflectance even varies for the same person throughout the course of a day, e.g., hot vs. cold skin, or dry vs. wet.

Properties of human skin have been measured and studied extensively in biomedical, cosmetic, and computer vision fields.

Analytic Skin Reflectance Models

Analytic reflectance models are frequently used because of their computational efficiency, Hanrahan and Krueger, "Reflection from layered surfaces due to subsurface scattering," Computer Graphics, SIGGRAPH '93 Proceedings, 165-174, 1993. They model a single scattering of light in skin composed of multiple smoothly bounded internal layers. That model was extended by adding an oil layer at the skin surface, Ng and Li, "A multi-layered reflection model of natural human skin," Computer Graphics International, 249-256, 2001.

Another model applies an analytic approximation to multiple subsurface scattering in skin with a rough surface, Stam, "An illumination model for a skin layer bounded by rough surfaces," Proceedings of the 12th Eurographics Workshop on Rendering Techniques, Springer, 39-52, 2001.

A physically-based multi-layer model for image synthesis uses biologically meaningful parameters, Krishnaswamy and Baranoski, "A biophysically-based spectral model of light interaction with human skin," Computer Graphics Forum 23, 331-340, September 2004.

Several skin modeling approaches use analytic bidirectional reflectance distribution functions (BRDFs), Blanz and Vetter, "A morphable model for the synthesis of 3D faces," Computer Graphics 33, Annual Conference Series, 187-194, 1999; Debevec et al., "Acquiring the reflectance field of a human face," Computer Graphics, SIGGRAPH 2000 Proceedings, 145-156, 2000; Haro et al., "Real-time, photorealistic, physically based rendering of fine scale human skin structure," Proceedings of the 12th Eurographics Workshop on Rendering Techniques, 53-62, 2001; Paris et al., "Lightweight face relighting," Proceedings of Pacific Graphics, 41-50, 2003; Tsumura et al., "Image-based skin color and texture analysis/synthesis by extracting hemoglobin and melanin information in the skin," ACM Transactions on Graphics, SIGGRAPH 2003, 22, 3, 770-779, 2003; and Fuchs et al., "Reflectance from images: A model-based approach for human faces," Research Report MPI-I-2005-4-001, Max-Planck-Institut fur Informatik, 2005.

The BRDF parameters can be estimated from reflectance measurements using non-linear optimization. Although a BRDF describes local light transport at each surface point, it ignores subsurface scattering, which is largely responsible for the appearance of skin.

Another analytic model uses bi-directional surface-scattering reflectance distribution function (BSSRDF), Jensen et al., "A rapid hierarchical rendering technique for translucent materials," Computer Graphics, SIGGRAPH 2002 Proceedings, 576-581, 2002; and Jensen et al., "A practical model for subsurface light transport," Computer Graphics, SIGGRAPH 2001 Proceedings, 511-518, 2001.

The BSSRDF describes the full effect that incident light has on reflected light from a surface patch around a point. The BSSRDF is eight-dimensional, assuming a two-dimensional parameterization of the surface. However, dense sampling of an eight-dimensional function is difficult using conventional techniques.

Non-Parametric Skin Reflectance Models

Another method estimates a non-parametric BRDF of a human face by combining reflectance samples from different points on the surface, Marschner et al., "Image-based BRDF measurement including human skin," Proceedings of the 10th Eurographics Workshop on Rendering, 139-152, 1999. They later extended this work by adding a detailed albedo texture, Marschner et al., "Modeling and rendering for realistic facial animation," 11th Eurographics Workshop on Rendering, 231-242, 2000. They observed that the BRDF of skin exhibits strong forward scattering at grazing angles that is uncorrelated with a specular direction.

A data-driven BRDF model is described by Matusik, et al., "A data-driven reflectance model," ACM Transactions on Graphics, SIGGRAPH 2003, 22, 3 (July), 759-770, 2003. That model estimates a non-parametric surface BRDF at each surface point. This introduces less error than imposing the behavior of a particular analytic BRDF model. More important, the data-driven BRDF model does not require non-linear optimization and leads to a more robust fitting procedure.

Image-Based Face Modeling

Image-based models have provided realistic representations for human faces. Image-based models easily represent effects such as self-shadowing, inter-reflections, and subsurface scattering, Pighin et al., "Synthesizing realistic facial expressions from photographs," Computer Graphics, vol. 32 of SIGGRAPH 98 Proceedings, 75-84, 1998.

Other image-based models allow variations in lighting, Georghiades et al., "Illumination-based image synthesis: Creating novel images of human faces under differing pose and lighting," IEEE Workshop on Multi-View Modeling and Analysis of Visual Scenes, 47-54, 1999; Debevec et al., "Acquiring the reflectance field of a human face," Computer Graphics, SIGGRAPH 2000 Proceedings, 145-156, 2000; and viewpoint, and expression, Hawkins et al., "Animatable facial reflectance fields," Rendering Techniques '04, Proceedings of the Second Eurographics Symposium on Rendering, 2004; and Cula et al., "Skin texture modeling," International Journal of Computer Vision 62, 1-2 (April-May), 97-119, 2005.

However, the memory requirement for image-based models is large. The measurement procedures are inefficient and assume non-local low-frequency lighting. Pure image-based representations are also inherently difficult to edit and modify.

Another model combines an image-based model, an analytic surface BRDF, and an approximation of subsurface scattering to create highly realistic face images for the movie 'Matrix Reloaded', Borshukov and Lewis, "*Realistic human face rendering for the Matrix Reloaded*," SIGGRAPH 2003 Conference Abstracts and Applications (Sketch), 2003.

A variant of that method for real-time skin rendering uses graphics hardware, Sander et al., "*Real-time skin rendering on graphics hardware*," SIGGRAPH 2004, Sketch, 2004.

U.S. Patent Application 20040150642, "Method for digitally rendering skin or like materials," filed by Borshukov and Lewis on Aug. 5, 2004, describes a method for rendering skin tissue. That method applies a blurring process to a two-dimensional light map.

Another image-based uses independent component analysis (ICA) to decompose images of faces into layers, e.g., melanin and hemoglobin, Tsumura et al., 2003. That method is capable of re-synthesizing new images of faces while adding effects such as tanning and aging.

A realistic skin reflectance model should be able to accommodate a wide variation of face appearance. The model should also allow a graphic artist to change the appearance of skin based on easy to interpret parameters, e.g., race, gender, or age. The model needs to incorporate measurements of real faces for rendering virtual duplicates. Images generated from the model, ideally in real-time, need to appear photorealistic from arbitrary viewpoints. And the model should allow easy modification and transfer of skin appearance.

SUMMARY OF THE INVENTION

The invention provides a system and method for rendering and editing images of realistic faces. In-vivo light reflection and subsurface scattering of faces of a large and diverse group of people varying in age, gender, race are measured. The faces are also measured with different external factors, such as cosmetics, temperature, and sweat.

Non-negative matrix factorization (NMF) is used to decompose a high-dimensional bi-directional scattering surface reflectance distribution function (BSSRDF) of skin into a low-dimensional model that can be estimated from measured data.

The skin reflectance model can be used in interactive and off-line rendering systems and generates results that substantially reproduce photographs of human faces.

User-defined parameters, such as gender, race, or tan, can be used to interpolate reflectance data to edit the appearance of a face in a synthesized image, for example, changing a Caucasian face to an Oriental face. It is also possible to edit local facial features, such as moles, freckles, and hair follicles.

DETAILED DESCRIPTION OF THE PREFERRED EMBODIMENT

Our invention provides a method and system for generating a skin reflectance model from bio-physical measurements of faces. Furthermore, the invention allows a user to edit the model, and to render novel images of faces.

Bio-Physically Skin Reflectance Model

Figure 1:
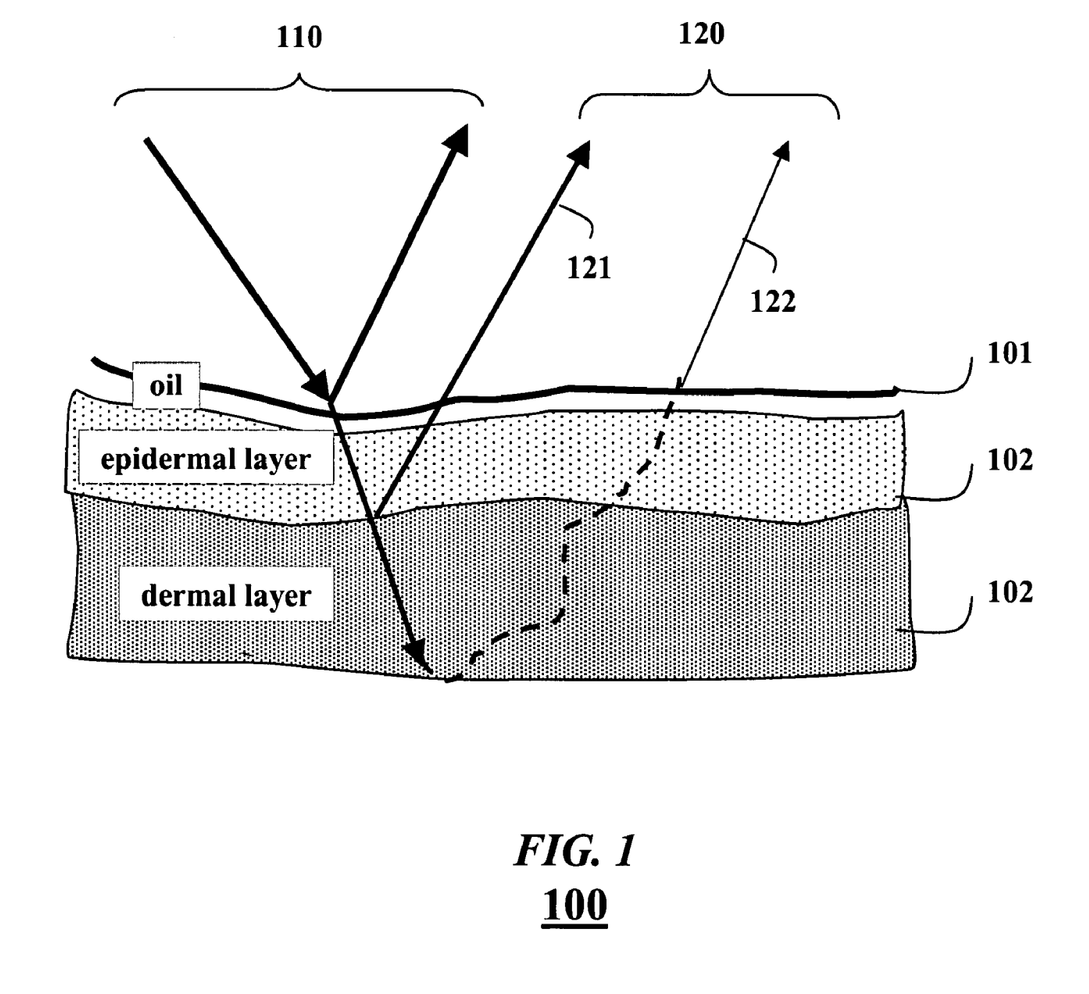
FIG. 1 is a schematic of a bio-physical skin reflectance model according to the invention.

As shown in FIG. 1, we describe overall skin reflectance as a sum of specular reflection 110 on a surface of skin due to an air-oil interface 101, and diffuse reflection 120 due to subsurface scattering. Most of the high-frequency spatial color variation in human skin is due to the epidermal layer, whereas strong light scattering in the dermal layer is a more slowly varying effect. Diffuse subsurface scattering is due to absorption 121 and light scattering 122 in the epidermal layer 102 and the dermal layer 103. The epidermis scatters light strongly and contains melanin along the interface to the dermis layer 103, which is highly absorbing. This absorption component is a local effect with high spatial variation across the face due to hair follicles, sweat glands, freckles, dimples, etc. Because the dermis includes blood, it is highly scattering in the red channel and strongly absorbing in the green and blue channels, mainly due to hemoglobin. The dermal light scattering is a non-local, slowly varying effect.

We model the light that is immediately reflected from the air-oil interface 101 layer with a spatially-varying bi-directional reflectance distribution function (BRDF). We partition the diffuse subsurface reflectance into two components. A diffuse albedo map expresses high-frequency color variations due to epidermal absorption and scattering, and a translucency map expresses low-frequency absorption and scattering in the dermal layer. Three-dimensional facial face geometry is represented by a normal map.

More formally, we denote the BSSRDF as $S(x_i, \omega_i, x_o, \omega_o)$, where $\omega_i$ is the direction of the incident illumination at point $x_i$, and $\omega_o$ is the observation direction of radiance emitted at point $x_o$. Similarly, we use $f_s(x_i, \omega_i, \omega_o)$ for the surface BRDF. The relative contributions of the surface reflectance and the diffuse reflectance due to subsurface scattering are modulated by Fresnel coefficients:

$$S_{skin} = F_t(\eta, \omega_i) S(x_i, \omega_i, x_o, \omega_o) F_t(\eta, \omega_o),$$

$$f_{skin} = F_r(\eta, \omega_i) f_s, \qquad (1,2)$$

where $F_r$ and $F_t = (1 - F_r)$ are the Fresnel coefficient at the air-skin boundary for both the incoming and outgoing radiance, and $\eta$ is the relative index of refraction between skin and air, i.e., $\cong 1.3$.

We model the subsurface scattering term S using a dipole diffusion approximation, while the specular BRDF components $f_s$ is modeled using a data-driven approach. The parameters of both the BSSRDF and the BRDF are estimated from measurements as described below.

Method Overview

Figure 2:
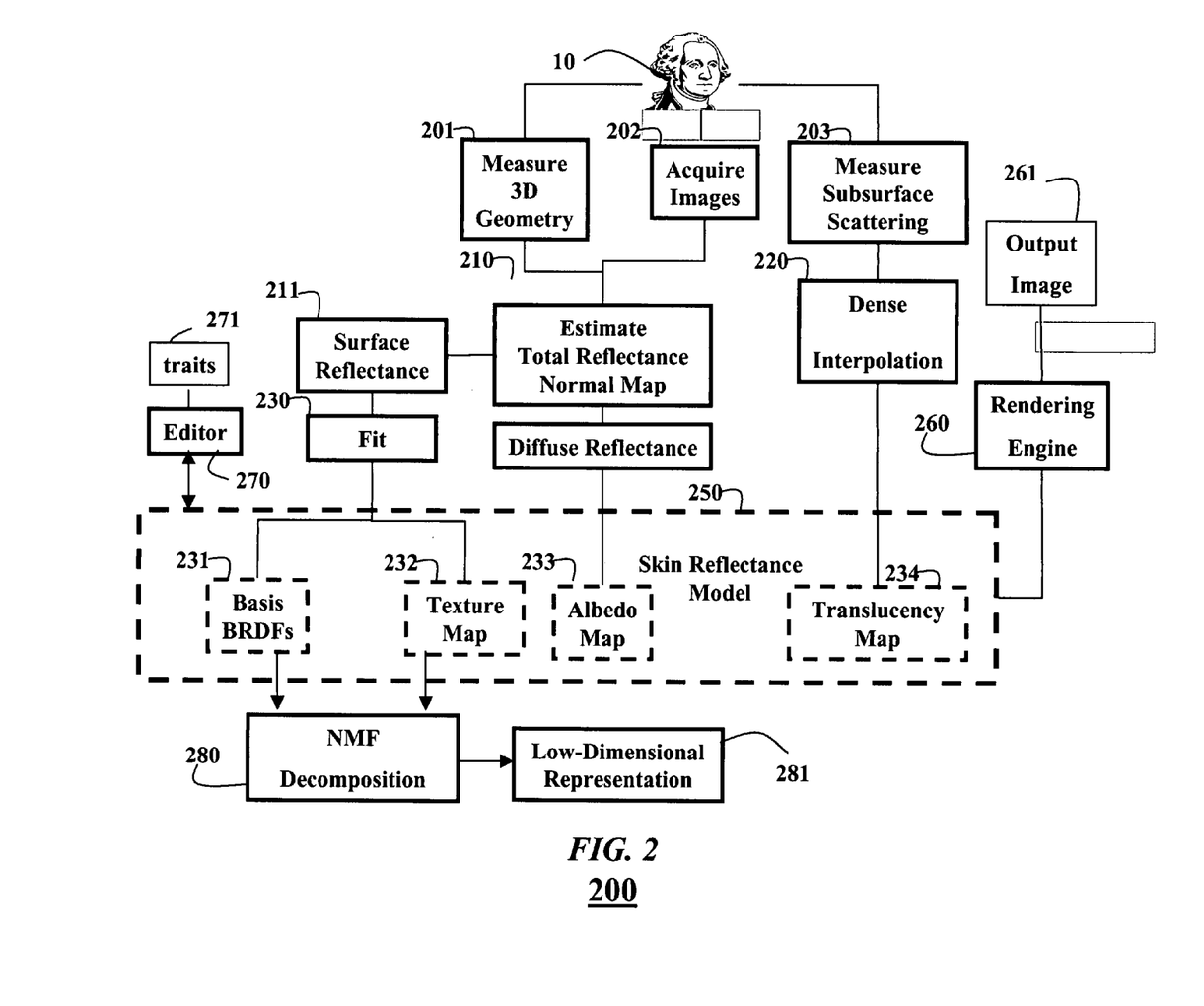
FIG. 2 is a flow diagram of a method for generating the skin reflectance model according to the invention.

FIG. 2 shows a computer implemented method 200 for generating a skin reflectance model according to our invention. Dashed blocks 231, 232, 233, and 234 are the parameters of our skin reflectance model 250. The method generates the model 250 from bio-physical measurement of a large, and varied collection of human faces. The method steps are performed for each face.

For each face, we measure 201 a 3D geometry of the face using a 3D scanner. Digital images from different viewpoints and with different illumination directions are acquired 202 of the face. The surface scan data and the image data are used to estimate 210 a total reflectance and a normal map. We scan 203 subsurface reflectance 203 using a fiber optic spectrometer 500 described in detail below with reference to FIG. 5. Using dense interpolation 220, we determine a translucency map 234. We separate total reflectance into two parts: Subsurface scattering 234 and 212 and (specular) surface reflectance 211.

We model subsurface scattering using the diffusion approximation by Jensen et al., "*A practical model for subsurface light transport*," Computer Graphics, SIGGRAPH 2001 Proceedings, 511-518, 2001. In accordance with Jensen et al., we use the term "diffuse reflectance" for reflection due to this diffusion process.

Surface reflectance is modeled using a monochrome BRDF representation. The monochrome assumption is motivated because skin is a dielectric.

The two components, diffuse reflectance $S(x_i, \omega_i, x_o, \omega_o)$ and surface reflectance $f_s(x_i, \omega_i, \omega_o)$, add up to the complete reflectance model:

$$f_r(x_i, \omega_i, x_o, \omega_o) = S(x_i, \omega_i, x_o, \omega_o) + f_s(x_i, \omega_i, \omega_o).$$

Diffuse reflectance $S(x_i, \omega_i, x_o, \omega_o)$ is the practical subsurface scattering model presented in Jensen et al. 2001, and is defined by the reduced scattering cross-section $\sigma_{s'}$ and the absorption cross-section $\sigma_a$. These are also known as $\mu_{s'}$ and $\mu_a$ in other fields. The values for $\sigma$ and $\mu$ are derived from the albedo map 233 and the translucency map 234.

We subtract the estimate diffuse reflectance from the measured total reflectance to obtain the surface reflectance 211. We fit 230 a set of densely-sampled BRDFs 231 to the surface reflectance 211. We determine 2D texture maps 232, of 2048×2048 resolution, to store the coefficients of the BRDF basis for each surface point. To map between the 3D face geometry and the 2D texture map, we use an area-preserving texture parameterization.

Next, we decompose 280 the high-dimensional BRDF basis using non-negative matrix factorization (NMF) to obtain a low-dimensional representation 281.

Therefore, the parameters of our reflectance model are the NMF BRDF basis 231, typically four, texture maps 241 with coefficients for the linear combination of BRDF basis, one albedo map 212, and one translucency map 221.

The following sections describe each of these processing steps in more detail.

Measuring Skin Reflectance

Figure 3:
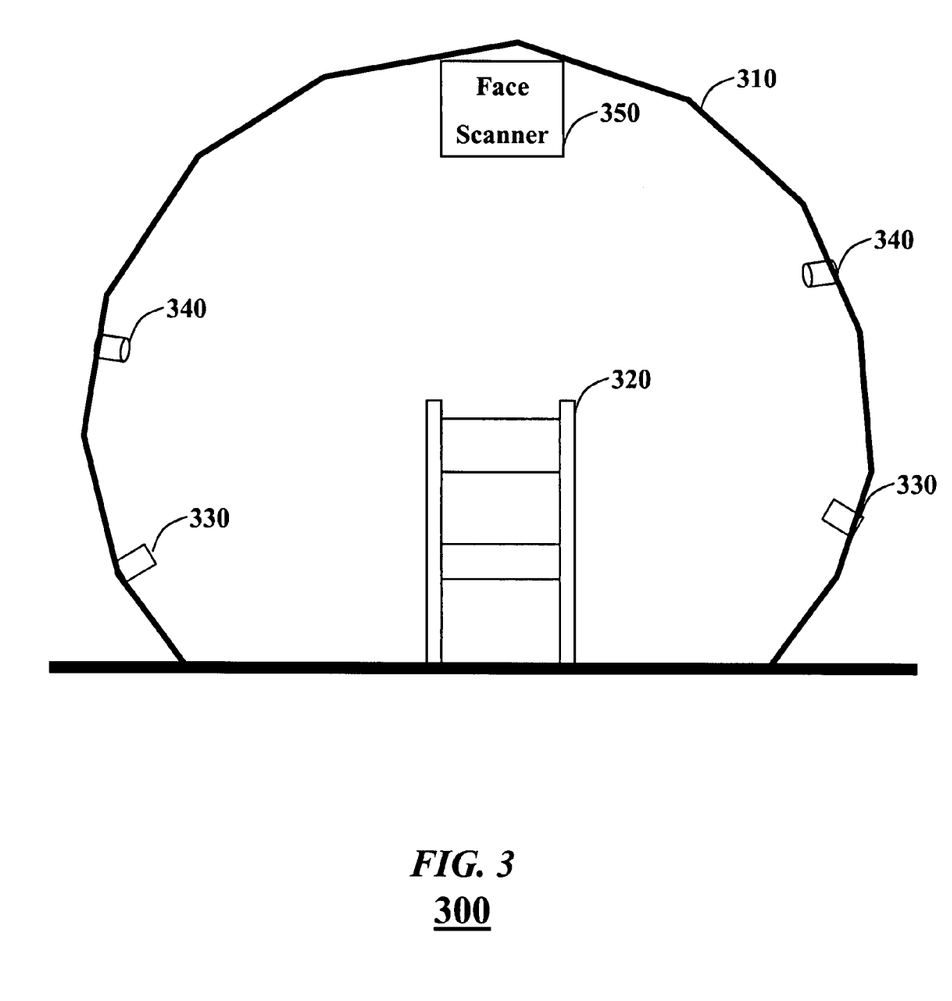
FIG. 3 is a schematic of a system for measuring skin reflectance data according to the invention.

As partially shown in FIG. 3, we measure 201 the 3D geometry and acquire the images using a system 300. The system includes a tubular frame 310 in the form of a geodesic dome. A chair 320 for the person being measured is placed inside the dome. Digital cameras 330 are mounted on the frame and aimed at the face from various viewpoints. The dome also includes LED light sources 340. We use 16 cameras and 150 LEDs.

During operation, the system sequentially turns each light on while simultaneously acquiring images with the cameras. We acquire high-dynamic range (HDR) images by repeating the acquisition sequence with different exposure settings.

Measuring 3D Geometry

A face-scanner 350 mounted in the dome includes two structured light projectors and four cameras. The output of the scanner is a polygon mesh containing about 40,000 triangles. The mesh resolves features as small as 1 mm. The mesh is cropping to remove non-facial areas and degenerate triangles.

Then, the mesh is refined using Loop-subdivision, Loop, "*Smooth Subdivision Surfaces based on Triangles*," Master's thesis, Department of Mathematics, University of Utah, 1987. This results in a high-resolution mesh with 500,000 to 1 million vertices. The subdivision implicitly removes noise.

We convert the high-resolution mesh to an unstructured list of point samples, i.e., surfels without connectivity, see U.S. Pat. No. 6,639,597, "Visibility Splatting and Image Reconstruction for Surface Elements," issued on Oct. 28, 2003 to Zwicker, et al., incorporated herein by reference. Each surfel stores the necessary information for image reconstruction using EWA splatting, Zwicker et al., "*Ewa splatting*," IEEE Transactions on Visualization and Computer Graphics 8, 3, 223-238, 2002.

From the image data, we determine a lumitexel for each surfel from the image reflectance samples. Each observed radiance value $L(\omega_o)$ is normalized by the irradiance $E_i(\omega_i)$ of the corresponding light source l to obtain a BRDF sample value $f_r$:

$$f_r(\omega_i, \omega_o) = \frac{L(\omega_o)}{E_i(\omega_i)} \quad (3)$$

We calibrate the BRDF measurements using Fluorilon, a material with know properties. All processing is performed on RGB data except where noted otherwise. We determine lumitexels in shadow areas by rendering the face from camera and light source viewpoints using EWA splatting, Zwicker et al., "*Surface splatting*," Computer Graphics, SIGGRAPH 2001 Proceedings, 371-378, 2001. EWA filtering guarantees that each surfel splat covers at least one pixel. The percentage of visible pixels per splat is approximated by the ratio of total rasterized pixels to effectively blended pixels. If this percentage is above a predetermined threshold, then we mark the surfel as visible from that camera or light source. This process of determining visibility and occlusion give similar results as shadow mapping.

On average, a lumitexel contains about 900 reflectance samples per color channel, with many lumitexels having up to 1,200 samples. The numbers vary depending on occlusions across the face.

In contrast with Marschner et al., Lensch et al., and Fuchs et al. 2005, see above, we collect enough samples for a reliable BRDF fit at almost all lumitexels, without clustering. The data for lumitexels with a badly conditioned fit are interpolated during generation of the texture maps 232.

Estimating Normal Map and Albedo Map

We estimate surface normals at each lumitexel from the reflectance data. For each camera viewpoint, we determine a direction of maximum reflectance by interpolation between the directions of the four brightest measurements. The half-way vector between this direction and the viewing vector is the surface normal estimate for this viewpoint. Then, we remove outliers from the set of normals from all viewpoints and interpolate the final surfel normals to obtain the normal map.

However, real-world reflections are off-specular, i.e., they are not necessarily aligned with a mirror direction. To improve the normal estimation further, we can use a photometric stereo method, Goldman et al., "*Shape and spatially-varying BRDFs from photometric stereo*," Tech. Rep. 04-05-03, University of Washington, 2003.

To separate the specular surface reflectance from the diffuse subsurface reflectance 203 at each surfel, we use the diffuse BRDF approximation of the BSSRDF:

$$S_{brdf}(x, \omega_i, \omega_o) = \frac{R_d}{\pi}, \quad (4)$$

where $R_d$ is the diffuse reflectance:

$$R_d = \frac{\alpha'}{2}\left(1 + e^{-\frac{4}{3}\frac{1+F_r}{1-F_r}\sqrt{3(1-\alpha')}}\right)e^{-\sqrt{3(1-\alpha')}}. \quad (5)$$

The diffuse reflectance $R_d$ depends only on a reduced albedo a', and the Fresnel terms. The BRDF approximation is equivalent to the full BSSRDF for a semi-infinite plane of homogeneous, almost opaque material under uniform incident illumination. Intuitively, under these assumptions we cannot distinguish if photons enter the surface, scatter, and reemit as diffuse light, or if the photons are immediately reflected at a point from a diffuse surface. We found this approximation to be relatively accurate for the diffuse reflectance component of our skin model. Any remaining error is a diffuse component in the surface BRDF.

We estimate $R_d$ at each surface point from the lumitexel data. Based on the assumption that we observe pure diffuse reflectance for at least some of the observation angles, we determine a maximum value $R_d$ that is less than or equal to the minimum of the BRDF sample values $f_r$. This is done by determining the minimum ratio between values $f_r$ and the unit diffusion reflectance:

$$R_d = \min_i \frac{\pi f_r(\omega_i, \omega_o)}{F_t(\eta, \omega_i)F_t(\eta, \omega_o)}. \quad (6)$$

We divide the observed BRDF sample values by the Fresnel coefficients in accordance with Equation (2), as we determine the diffuse component using the BSSRDF. In order to reduce outliers and the influence of motion artifacts, we determine a stable minimum by penalizing grazing observations and discarding the k smallest values. The $R_d$ values for each surface point are re-parameterized and interpolated into the albedo map 233.

Determining a Basis for Surface BRDFs

An interface reflection is determined from each lumitexel by subtracting the diffuse reflectance 203 from the overall reflectance in the image data: $R_i = R - R_d$. Instead of fitting an analytic reflectance model to this data, we use the data-driven BRDF model of Matusik et al. 2003, see above. The object is to express the data $R'_i$ as a linear combination of densely measured BRDF basis. We use 59 BRDF basis of dielectric materials that are related to human skin, such as paints, fabrics, organic materials, and leather. Each BRDF consists of over four million samples.

To account for the area of the light source, we convolve each BRDF basis with a disk-shaped filter kernel. This works because each light source spans approximately the same solid angle when viewed from any point on the face.

An angle between illumination direction and surface normal is $v_1$. Rather than normalizing the observed reflectance samples by dividing the samples by cos $v_1$, we multiply the BRDF basis by this factor. This minimizes the influence of noise and quantization artifacts at grazing angles.

We have n observed reflectance samples $R_i(\omega^i_i, \omega^i)$ and m BRDF basis $M_j$. We construct an n×m matrix M, where the elements in the $i^{th}$ row and $j^{th}$ column are:

$$M_{ij} = \cos v_i M^j(\omega_i^i, \omega_o^i). \quad (7)$$

We solve for the vector x according to:

$$Mx = R \text{ s.t.} x_i \geq 0, \quad (8)$$

where R is an n×1 column vector with elements $R_i$. We use quadratic programming to solve this over-constrained least-squares problem. The resulting $x_i$ are the coefficients of the linear combination of BRDF basis that best reproduce the lumitexel data. We constrain the coefficients to be positive to get stability of the solution. To further improve our results, we take the cubic root of the elements in the matrices M and R. This transforms the BRDF basis and reflectance values into a more perceptually appropriate space where highlights are not oversaturated. Highlights on dielectric materials like skin are of the same color as the light source, i.e., white.

Consequently, we can use monochrome BRDF basis. This reduces the degrees of freedom by a factor of three and increases the stability of the fit. The 59 BRDF basis are not specific to human skin. The basis are capable of representing reflectance of a much wider range of materials. We use dimensionality reduction to determine a smaller linear basis that is specific to human skin. We apply NMF to the vector x of positive coefficients at each surface point independently. Unlike principle-component analysis (PCA), the NMF basis is not orthogonal. However, the original data can be expressed as positive linear combinations of the NMF basis vectors. That is, when fitting reflectance data to the reduced NMF basis, we can still perform non-negative least squares optimization.

Figure 4:
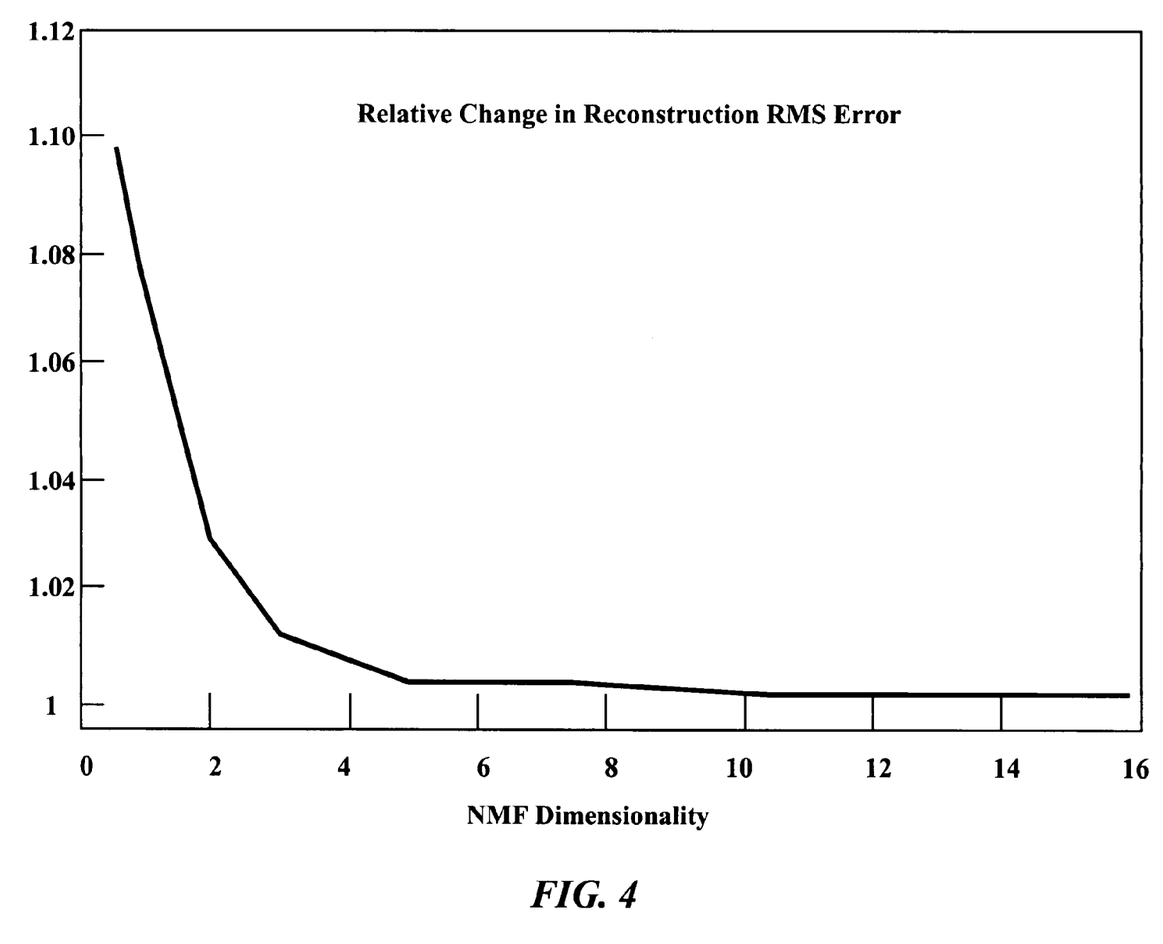
FIG. 4 is graph of a reconstruction root mean square error as a function of a number of bi-directional reflectance distribution function basis.

As shown in FIG. 4, we plot the reconstruction root mean square (RMS) error as a function of the number of NMF BRDF basis to determine the smallest NMF basis that are necessary to represent the data. The plateau for a single face is reached around four BRDF basis, after which the relative reconstruction error is relatively constant. The results do not improve much beyond four NMF BRDF basis. The coefficients for each surface point are stored in four BRDF coefficient texture maps 232. In addition, we store four NMF BRDF basis per face.

Measuring Translucency

Figure 5:
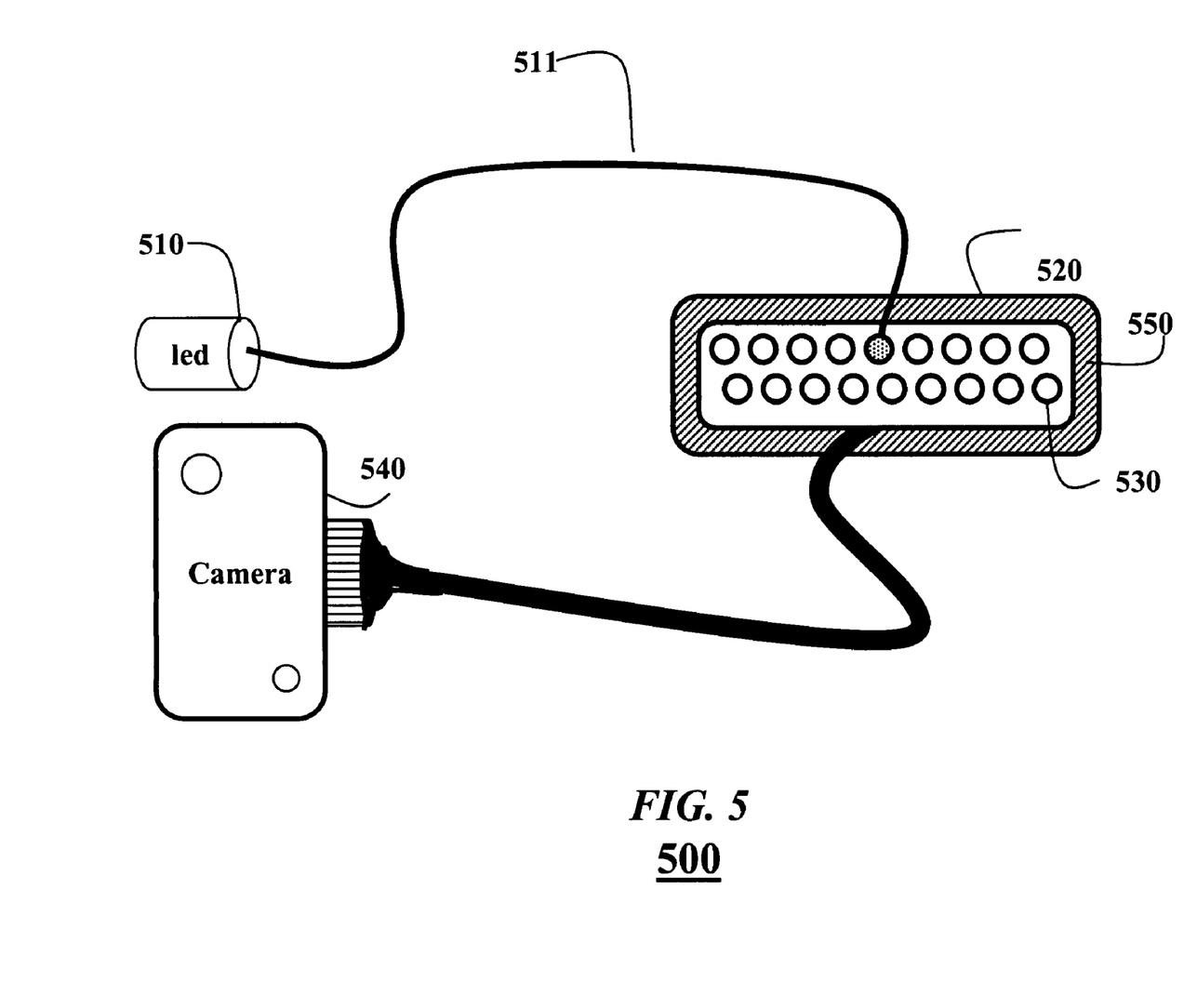
FIG. 5 is a block diagram of a subsurface reflectance measurement apparatus according to the invention.

As shown in FIG. 5, our subsurface reflectance measurement apparatus 500 is an image-based version of a fiber optic spectrometer with a linear array of optical fiber detectors. Light from a white LED 510 is coupled to a source fiber 511 terminating in a sensor head 520. The sensor head also holds multiple detection fibers 530. The alignment of the fibers is linear to minimize a size of the sensor. A digital camera 540 records light collected by the detector fibers.

Pressure variations on the skin caused by mechanical movement of the sensor head 520 influence the results. To maintain constant pressure between skin and sensor head, we attached a silicone membrane 550, which is connected to a vacuum pump, not shown. This greatly improves the repeatability of the measurements when the head is pressed against the skin. We select three points where the sensor head 520 can be placed reliably, the forehead, cheek, and below the chin.

We acquire multiple images bracketed by two to three 3 f-stops to determine an HDR image of the ends of the detection fibers.

Although some areas of the human body, e.g., the abdomen, exhibit anisotropic subsurface scattering, the diffuse subsurface scattering of facial skin can be well approximated with an isotropic scattering model. Therefore, we measure only a one-dimensional profile and assume rotational symmetry. We fit an analytic BSSRDF model to the data points of each subsurface measurement. This provides us with reduced scattering coefficient $\sigma_s'$ and absorption coefficient $\sigma_a$. These parameters also express high-frequency albedo variations, e.g., redness and freckles.

It is impractical to densely measure these parameters across the entire face using our sensor head. Therefore, we use high-resolution images to estimate the diffuse albedo map 233, and use the spectrometer to measure slowly varying translucency.

From the measured $\sigma_a$ and $\sigma_s'$, we derive an effective transport coefficient:

$$\sigma_{tr} = \sqrt{3\sigma_a(\sigma_a+\sigma_s')} \sim 1/l_d, \quad (9)$$

where $l_d$ is the diffuse mean free path. The path $l_d$ or $1/\sigma_{tr}$ provides a measure of skin translucency. There is little variation across a face. We interpolate $1/\sigma_{tr}$ from the three measurements to obtain the dense translucency map 234 for the face.

Rendering

For off-line rendering 260 an output image 261 with are skin reflectance model 250, we use a Monte Carlo ray tracer. For interactive rendering with arbitrary BRDFs, we use separable approximations. In either case, input to the rendering engine are the four NMF BRDF basis 231, the four texture maps with the coefficients of the NMF BRDF basis 232, the albedo map ($R_d$) 233, and the translucency map ($1/\sigma_{tr}$) 234.

We transform the $R_d$ values of the albedo map to apparent albedo values a' by inverting Equation (5). We derive the model parameters $\sigma_s'$ and $\sigma_a$ from $\sigma_{tr}$:

$$\sigma_s' = a'\sigma_t' \text{ and } \sigma_a = \sigma_t' - \sigma_s', \text{ with } \sigma_t' = \sigma_{tr}/\sqrt{(3(1-a'))}.$$

Surface reflectance at each surface point is determined using a linear combination of the NMF BRDF basis 231.

Skin Reflectance Analysis

Our skin reflectance model treats each reflectance component independently. This enables us to render or edit each component without affecting the other components. Consequently, we analyze each component separately and do not consider the correlation between them.

Analysis of Surface BRDFs

Surface BRDFs express monochrome light reflection at the air-oil layer 101. The BRDFs can be represented with a low-dimensional NMF basis of densely-sampled BRDFs. The effect of the surface BRDF on overall appearance is relatively pronounced, especially for different external conditions. Our analysis indicates that BRDFs representing skin are a small subset of all isotropic BRDFs.

Analysis of Diffuse Albedo Maps

The diffuse albedo is the component of our model that captures most of the intra-personal and extra-personal variations. Small-scale intra-personal albedo variations are due to skin imperfections, markings, scars, etc. and typically show high spatial frequency across the face. Overall extra-personal albedo variations are mainly due to race, gender, tanning, or other external factors. We first transform all albedo maps in each dataset into a common and decorrelated color space.

An albedo map bears many similarities to a stochastic image texture. Consequently, we apply the texture analysis method of Heeger and Bergen, "*Pyramid-based texture analysis/synthesis*," Proceedings of SIGGRAPH 95, Computer Graphics Proceedings, Annual Conference Series, 229-238, 1995.

We determine statistics, e.g., histograms, the original albedo map at full resolution, and of filter responses at different orientations and scales organized as a steerable pyramid. We use seven pyramid levels with four oriented filters, and down-sample the albedo map by a factor of two at each level. Each histogram has 256 bins. The histograms of all filter responses including a low-pass and a high-pass and the histogram of the original albedo map are concatenated into a 256×31×3=23,808 element vector H. This vector can be viewed as a generative model of a texture for a given person. For example, we can use this vector for albedo transfer between two subjects using histogram matching.

To analyze the extra-personal variations, we resample the albedo maps of into a common (u, v) parameter space using point and radial basis function interpolation, Pighin et al. 1998. To obtain reliable statistics, we cluster points in corresponding face regions. Currently, we only specify beard versus no-beard regions, but we could use a finer granularity and distinguish between chin, cheek, forehead, nose, eyelid, and beard areas.

For each face i and each region r, we construct a histogram vector $H^r_i$ as described above. All vectors $H^k_i$ for a specific region k are stored as column vectors in a matrix $M_h$. Then, we can apply principal component analysis (PCA) on the matrix $M_h$ to determine a region-specific basis for the albedo map histograms. Each point in this reduced space corresponds to the albedo of a particular person. We use this PCA basis to synthesize new albedo maps, which can be used for image synthesis.

Analysis of Translucency

Translucency component accounts for non-local subsurface scattering in the epidermis and dermis layers 102-103. The translucency component is a slowly varying effect that is responsible for much of the red color and soft shadows in human faces. It is important to note that translucency cannot be estimated directly from images. Therefore, we acquire the subsurface measurements with the spectrometer.

Overall, translucency values do not vary much between measurement points and between individuals. In practice, one could approximate it using a single value for the whole face. We define translucency as $1/\sigma_{tr}$.

Model Editing

We define meaningful parameters for editing 270 our skin reflectance models 250. The user assigns a set of arbitrary traits 271 to each face using a binary classification, i.e., trait present or not. Traits can include normal, cold, hot, sweat, lotion, makeup, powder, Asian, Caucasian, male, female, age, tan, etc.

The user can select a model of a face and change the reflectance properties according to any of the defined traits, e.g., making a face look more tanned. We apply this general idea to surface BRDFs and albedo maps. The translucency maps can be handled in a similar way, if desired.

We use mean differences to traverse the low-dimensional spaces of surface BRDFs using their NMF basis, and albedo histograms using their PCA basis. We determine an average of the basis vectors in each complementary pair of clusters associated with a trait, i.e., those faces with, and those without the trait. Differences between the complement averages provide trait vectors that can be used to interpolate between traits.

That is, we use convex combinations of trait vectors and apply the combinations to the data of a source face. Specifically, we determine trait vectors for the NMF basis of surface BRDFs. To determine a new target BRDF, we apply a linear combination of the trait vectors to the BRDF coefficients of the source face.

For albedo map changes, we determine trait vectors using the PCA basis of albedo histograms. A linear combination of trait vectors is applied to a basis histogram vector H of a source face, resulting in a target histogram vector H'. Then, we apply a histogram-matching technique to match H to H'. We use the basis histograms of the whole albedo map, or the basis histogram of facial regions, e.g., beard versus no-beard regions. For most applications, it makes more sense to start from original albedo map. To allow for sufficient variation during histogram matching, we add some noise to the source albedo map before we determine the histogram vector H.

Effect of the Invention

The invention provides a simple and practical skin reflectance model that is powerful enough to represent most aspects the appearance of facial skin. The invention combines an analytic model for subsurface scattering with a low-parameter non-parametric BRDF model. An important feature of the model according to the invention is that all parameters of the model can be estimated from measurements.

Images rendered from our skin reflectance model reproduce photographs of real human faces taken under arbitrary illumination and pose.

The invention also enables editing facial reflectance. To accomplish this, the invention provides intuitive user parameters such as age, race, gender, and tan level, for example. The invention can be extended to model reflectance of other important parts of the face, such as the eyes, lips, and teeth.

We claim:

1. A computer implemented method for generating a skin reflectance model of a face, comprising:
   scanning a face to obtain a three-dimensional geometry;
   acquiring a plurality of images of the face;
   measuring subsurface scattering of the face;
   determining a translucency map from the subsurface reflectance;
   estimating a total surface reflectance and a normal map from the three-dimensional geometry and the plurality of images;
   estimating diffuse reflectance using the total reflectance;
   determining an albedo map from the diffuse reflectance;
   subtracting the diffuse reflectance from the total reflectance to obtain a surface reflectance;
   fitting a set of bi-directional reflectance functions to the surface reflectance;
   combining the set of bi-directional reflectance distribution functions, the albedo map, and the translucency map to form a skin reflectance model of the face; and
   rendering the skin reflectance model of the face as an output image of the face.

2. The method of claim 1, further comprising:
   decomposing the set of bi-directional reflectance functions into a set of bi-directional reflectance function bases and a set of texture maps storing coefficients of the set of bi-directional reflectance functions, and in which the decomposing is determined from the surface reflectance, the normal map, and the bi-directional reflectance function basis.

3. The method in claim 2, in which the set of bi-directional reflectance function bases are measured data.

4. The method in claim 2, in which the set of bi-directional reflectance function bases are determined from measured data using a non-negative matrix factorization.

5. The method of claim 1, in which the skin reflectance model is generated for a plurality of faces.

6. The method of claim 1, in which the plurality of images are acquired from different viewpoints and with different illumination directions.

7. The method of claim 1, in which the subsurface reflectance is measured with a fiber optic spectrometer.

8. The method of claim 1, in which the plurality of images have a high-dynamic range.

9. The method of claim 1, in which the 3D geometry is a mesh of triangles.

10. The method of claim 9, further comprising:
    converting the mesh of triangles to an unstructured list of surfels.

11. The method of claim 10, further comprising:
    determining a lumitexel for each surfel.

12. The method of claim 1, further comprising:
    defining a set of traits of the face;
    editing the model according to the set of traits.

* * * * *